United States Patent [19]

Kadin et al.

[11] Patent Number: 4,629,536

[45] Date of Patent: Dec. 16, 1986

[54] MULTILAYER DEPTH PROFILE METHOD

[75] Inventors: Alan M. Kadin, Troy; Robert W. Burkhardt, Birmingham, both of Mich.

[73] Assignee: Energy Conversion Devices, Inc., Troy, Mich.

[21] Appl. No.: 710,924

[22] Filed: Mar. 12, 1985

[51] Int. Cl.$^4$ ............................................. G01N 27/20
[52] U.S. Cl. ..................................... 204/1 T; 204/434
[58] Field of Search ......................... 204/1 T, 42, 434

[56] References Cited

U.S. PATENT DOCUMENTS

| | | | |
|---|---|---|---|
| 2,319,196 | 5/1943 | Anderson et al. | 204/434 |
| 2,457,234 | 12/1948 | Herbert et al. | 204/434 |
| 2,603,595 | 7/1952 | Rondel | 204/434 |
| 3,975,681 | 8/1976 | Angelini et al. | 204/434 |
| 4,160,702 | 7/1979 | Baxter | 204/434 |
| 4,310,389 | 1/1982 | Harbulak | 204/434 |
| 4,495,558 | 1/1985 | Cath et al. | 204/1 T |

FOREIGN PATENT DOCUMENTS 0838313  6/1981  U.S.S.R. ............................. 204/1 T

OTHER PUBLICATIONS

J. Perriére, S. Rigo and J. Siejka; "Investigation of Cation-Transport Processes During Anodic Oxidation of Duplex Layers of Tantalum on Niobium by the Use of Rutherford Backscattering and Nuclear Microanalysis"; J. Electrochem. Soc.: Solid-State Science and Technology; Sep. 1978; pp. 1549-1557.
D. W. Palmer and S. K. Decker; "Microscopic Circuit Fabrication on Refractory Superconducting Films"; Rev. Sci. Instrum., vol. 44, No. 11, Nov. 1973, pp. 1621-1624.
H. Kroger, L. N. Smith and D. W. Jillie; "Selective Niobium Anodization Process for Fabricating Josephson Tunnel Junctions"; Appl. Phys. Lett. 39(3), Aug. 1, 1981; pp. 280-282.
J.P.S. Pringle; "The Anodic Oxidation of Superimposed Niobium and Tantalum Layers: Theory"; Electrochimica ACTA, vol. 25, 1980, pp. 1403-1421.
J.P.S. Pringle; "The Anodic Oxidation of Superimposed Metallic Layers: Theory"; Electrochimica ACTA, vol. 25, 1980, pp. 1423-1437.

Primary Examiner—Terryence Chapman
Attorney, Agent, or Firm—James D. Ryndak; Lawrence G. Norris; Richard M. Goldman

[57] ABSTRACT

Methods are provided for analyzing multilayer structures. The multilayer structure is electrolytically anodized at constant current through a plurality of layers of the structure over a predetermined surface area. During the anodization, the change of the anodization voltage or a time derivative thereof as a function of time is monitored as the anodization through the layers occurs to obtain data. The data may be analyzed in several ways to determine whether degradation of the multilayer structure has occurred, to determine the number of layers present in the multilayer structure and to determine the layer thickness of the multilayer structure.

The disclosed methods are accurate, inexpensive and rapid.

31 Claims, 5 Drawing Figures

# MULTILAYER DEPTH PROFILE METHOD

FIELD OF THE INVENTION

This invention relates to analyzing multilayer structures. More particularly, the invention relates to the depth profiling of multilayer structures for determining whether degradation has occurred and also for determining the number of layers and thickness of the multilayer structure.

BACKGROUND

Multilayer materials made up of a plurality of layers of different material are become increasingly important and are finding use in many different areas. These areas include, for example, X-ray optics coatings, superconducting materials, decorative and wear resistant coatings, catalytic materials and semiconductor materials. The layers in such materials may range, for example, from several angstroms (10,000 angstroms = 1 micrometer) to several hundred angstroms or more in thickness. Such multilayer materials may comprise a regular repetition of layers where, for example, repeating layers have the same composition, thickness and spacing. The multilayer material may comprise an irregular repetition of layers where repeating layers have a different layer thickness.

Determining the structure of such multilayer materials is necessary to assess performance, to check reliability and for quality control, for example, and for otherwise evaluating these materials. It is desirable to determine the number of layers, layer thickness, whether the structure has been degraded as a result of heating and whether the layer spacing is uniform, for example. Thus, an effective, rapid and low cost analytical technique is needed for the analysis of such multilayer materials.

While several methods are known which can be used to analyze multilayer structures, each has limitations rendering its use impractical in many applications.

Auger spectroscopy is a surface technique in which electrons bombard the surface of the material to be analyzed, inside an ultra high vacuum chamber. In response, the surface emits characteristic electrons. These characteristic electrons are then measured with an energy sensitive sensor. The Auger technique can be combined with ion sputter etching to remove material at the surface and analyze the new surface by the Auger technique. However, this technique is subject to certain limitations and inaccuracies because mixing and resputtering at the surface of the sample can result in compositional changes. In addition, preferential sputter etching can occur which also changes the surface composition.

Secondary ion mass spectroscopy (SIMS) is similar to the Auger technique except that ions are utilized instead of electrons. SIMS is thus another surface technique and requires ion sputter etching of the surface with the same attendant problems previously described.

X-ray fluorescence can be utilized to provide an average composition and can be used in conjunction with X-ray diffraction techniques. However, conventional X-ray equipment requires a total sample thickness of several thousand angstroms.

Rutherford backscattering is a process by which helium atoms are bombarded at very large energies into a sample. Some of these ions are backscattered and by a complex computer unfolding process it is possible to obtain a depth profile. Complicated and expensive equipment is required for this process.

A need exists for a multilayer profile technique that is simple, inexpensive, rapid and provides excellent resolution.

SUMMARY OF THE INVENTION

In accordance with one aspect of the present invention, a method is provided for determining whether degradation of an anodizable multilayer structure has occurred. In accordance with this aspect of the present invention, the multilayer structure is electrolytically anodized at constant current through a plurality of layers of the structure over a predetermined surface area of the structure. During the anodization, the change of the anodization voltage or a time derivative thereof as a function of time is monitored as the anodization proceeds through the layers to obtain data. The anodization voltage is the voltage applied across the anodization cell. The modulation of the anodization voltage or a time derivative therof of the data is compared to data obtained from the anodization at constant current under similar conditions through a plurality of layers of a reference multilayer structure, similar to the multilayer structure being tested and known to have no degradation.

It is believed that anodization proceeds by electrical oxidation in a fairly uniform, progressive manner through the material. As the anodization proceeds through a material, the anodization voltage increases.

When a multilayer structure is subjected to heat, for example, migration between layers can occur thereby causing degradation or a decrease in the sharpness of the multilayer structure layer interfaces. As used herein, "degradation" means a relative lack of a sharp interface between layers. This can occur as the structure is being manufactured or after it is made, such as by exposure to excessive heat or energy, for example. Degradation decreases the modulation of the anodization voltage or a time derivative thereof as a function of time. The decreased modulation indicates semiquantitatively that degradation of the multilayer structure has occurred or that the structure has been improperly manufactured.

In accordance with another aspect of the present invention, a method of determining the number of layers of an anodizable multilayer structure is provided. In accordance with the method, the multilayer structure is electrolytically anodized at constant current through the layers of the structure over a predetermined surface area. As the anodization through the layers of the structure occurs, the change of the anodization voltage or a time derivative thereof as a function of time is monitored to obtain data. The data is analyzed by counting each change in the anodization voltage or time derivative thereof that occurs as a result of anodizing from one layer into another layer to thereby determine the number of layers of said structure.

In accordance with another aspect of the present invention, a method of determining the thickness of an anodizable multilayer structure is provided. In accordance with the method, the multilayer structure is electrolytically anodized at constant current through the layers of the structure over a predetermined surface area of the structure. As the anodization through the structure occurs, the change of the anodization voltage or a time derivative thereof as a function of time is monitored to obtain data. The thickness of the multilayer structure is determined by comparing the data to reference data obtained under similar conditions from anodizing a known sample multilayer structure.

BRIEF DESCRIPTION OF THE DRAWINGS

The present invention can be more completely understood by reference to the accompanying drawings in which.

DETAILED DESCRIPTION

Figure 1:
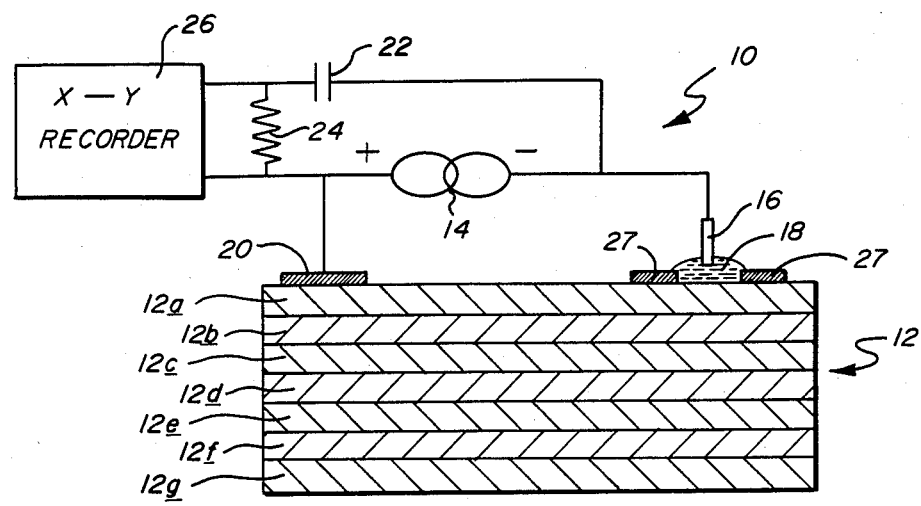
FIG. 1 is a schematic diagram of an anodization circuit used in accordance with the present invention.

Referring now to the drawings generally and in particular to FIG. 1, there is illustrated a schematic diagram of an anodization circuit 10 shown in electrical contact with an anodizable multilayer structure 12.

Anodization circuit 10 includes a dc source of electric current 14, a cathode 16, an electrolyte 18, an electrical contact 20, a capacitor 22, a resistor 24 and an x-y recorder 26. Electrical contact 20 provides good electrical contact to that portion of the film immediately beneath electrolyte 18.

Source of electric current 14 provides a constant dc current source to cathode 16. The layer of multilayer structure 12 that is being anodized functions as the anode Typical current densities can be relatively low, such as about 30 microamperes/square millimeter of surface area. The current density should be adjusted for the particular material. If the current density is too great, electrolysis at the surface (for example, evolution of gaseous oxygen) may occur. If the current density is too low, undercutting of the material may occur.

The surface area of multilayer structure which electrolyte 18 contacts defines the area of the anodization front as it advances through multilayer structure 12. A mask 27 defines the surface area which electrolyte 18 contacts and may comprise photoresist, tape or other material suitable for defining an area for contact by the electrolyte. A very small area, such as on the order of several square millimeters can be anodized, for example. The anodization through the multilayer structure has been found to be uniform in a direction parallel to the layers, and is somewhat self-correcting, since if one location oxidizes faster, it generally proceeds at a slower rate thereafter. As the anodization front proceeds through the structure, the voltage increases.

Figure 3:
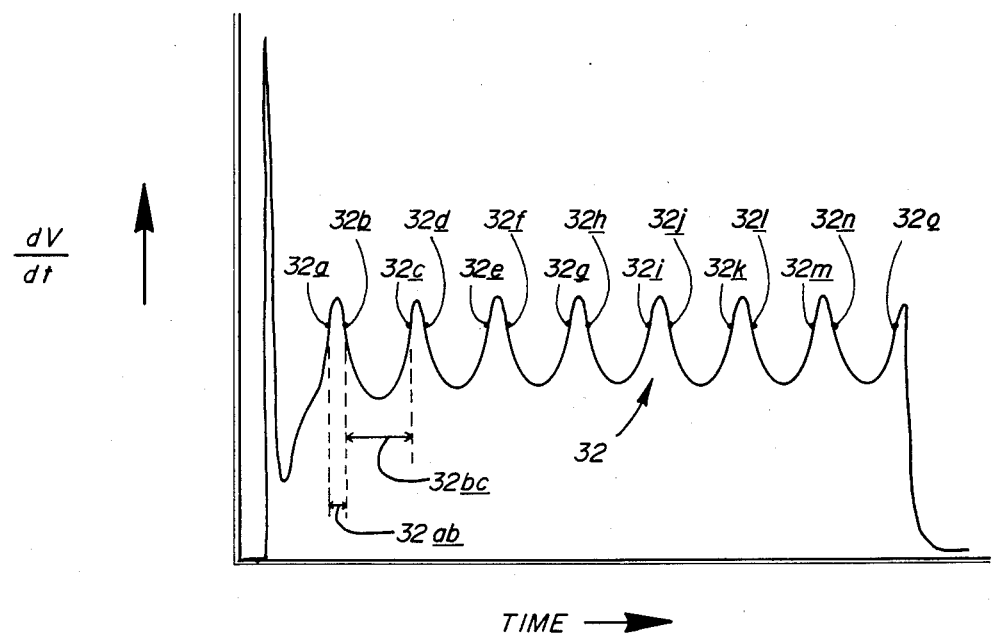
FIG. 3 is a graph illustrating the first time derivative of the anodization voltage as a function of time for the actual anodization of FIG. 2.
Figure 5:
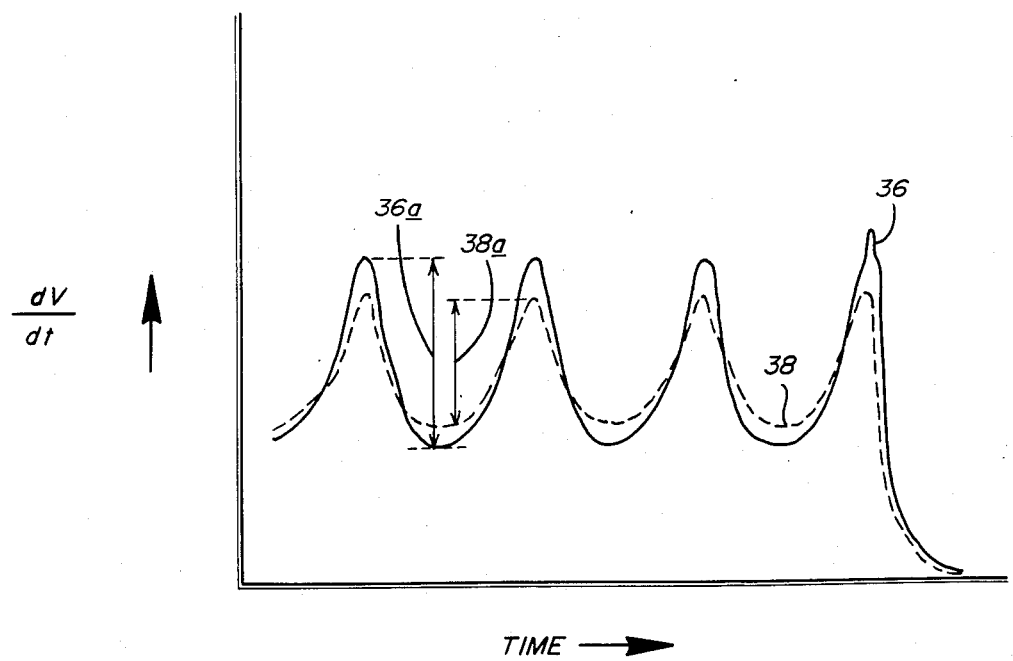
FIG. 5 is a graph illustrating the first time derivative of the anodization voltage as a function of time for the anodization of two multilayer structures, one of which has been subject to heat degradation.

The time derivative of the voltage across source of electric current 14 is monitored by x-y recorder 26 through a derivative circuit that includes capacitor 22 and resistor 24. In place of the x-y recorder, the following apparatus may be used, for example: a chart recorder (records one or more variables as a function of time), or a data logger (periodically registers data). During anodization through anodizable multilayer structure 12, a plot of the time derivative of the voltage versus time is recorded by x-y recorder 26, such as illustrated in FIGS. 3 and 5. This records the passage of the anodization front through the multilayer sample. The anodization front moves relatively rapidly through the multilayer structure. For example, rates of about 250 angstrom/minute are common. Thus, anodization through an entire sample may be on the order of several minutes or less.

The material of cathode 16 can be any suitable type. Gold is a preferred material since it does not corrode.

As used herein, the term "anodizable" means that the material can be electrolytically anodized and a soluble oxide is not produced by the electrolytic anodization. "Anodizable" material also includes material which may be present as an oxide in the multilayer structure prior to anodization of the structure but through which the anodization front can pass.

Anodizable multilayer structure 12 consists of a plurality of anodizable layers of material, 12a–12g. The layers can be relatively thin, such as in the range of about 5–25 angstroms. Thicker layers can, of course, also be analyzed. As used herein, "multilayer structure" refers to a structure having a plurality of compositionally different layers.

The electrolyte should be chosen so that the oxide formed by the anodization does not dissolve. One especially useful electrolyte is a water and ethylene glycol solution of ammonium pentaborate. The pH of the electrolyte can be adjusted as desired by addition of an acid. Since the electrolyte can affect the anodization rate, the same electrolyte should be used in the anodization of a reference multilayer structure and a test multilayer structure. Some materials, such as tungsten, anodize better in an electrolyte having a pH of about 3. Other materials, such as niobium, silicon and hafnium, anodize well at a pH of 3 or a pH of 6, for example. The effect of electrolyte pH on the anodization process can be easily determined merely by carrying out the anodization process at various pH levels.

Since the anodization rate is slightly temperature dependent, the anodization of the test and standard materials is preferably performed at about the same temperature.

A wide range of materials can be analyzed in accordance with the invention. For example, many multilayer combinations of the following elements can be analyzed: Group I metals, copper, silver and gold; Group II metals such as zinc and beryllium; Group III metals, such as aluminum, yttrium, lanthanum, cerium, praseodymium, neodymium, samarium, gadolinium and gallium; Group IV metals, such as titanium, zirconium, hafnium and tin; Group V metals, such as vanadium, niobium, tantalum, antimony and bismuth; Group VI metals, such as molybdenum, tungsten and uranium; and semiconductors such as aluminum arsenide, gallium phosphide, gallium arsenide, gallium antimonide, indium phosphide, indium arsenide, indium antimonide, germanium and silicon. Some combinations of the foregoing materials may be difficult to anodize. Some materials may require electrolytes that are different from what other materials require for anodization, for example. By way of example only, several combinations of layers which have been tested include: Nb/W; Hf/Si; W/Si; Nb/Si; and Ti/W.

The total sample thickness and the resistivity and thickness of individual layers can be a limiting factor. The sample thickness that can be analyzed can be limited by the compliance of the power supply. If the resistivity of the oxidized material becomes too great as the anodization front proceeds through a sample, the maximum permissible voltage could be reached. Also, a sufficiently high applied voltage could cause the layers to degrade.

Figure 2:
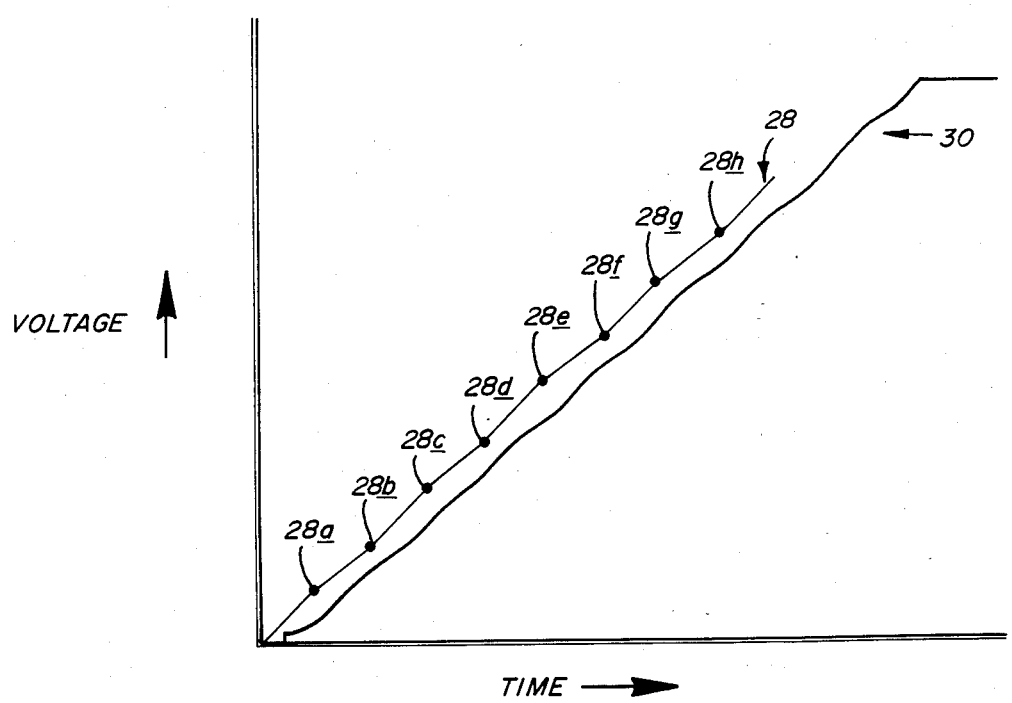
FIG. 2 is a graph illustrating the anodization voltage as a function of time for anodization of a theoretical and actual multilayer structure.

Referring to FIG. 2, there are illustrated two plots of voltage versus time of electrolytic anodization through multilayer structures. Line 28 illustrates a theoretical system of alternating layers of material A and B where the transition from one layer to the next layer is perfectly defined. There is no interdiffusion between layers and the layers are perfectly uniform and flat. The change in the slope of line 28 at points 28a-28h each define the end of one layer and the beginning of another layer of different material.

In actual practice, there will be some interdiffusion among layers and the layers will not be perfectly uniform and flat. Line 30 is an actual graphical representation of the voltage versus time plat for the anodization of a sample having alternating layers of niobium and tungsten, each of the layers having a nominal thickness of 20 angstroms. As illustrated by line 30, the change in the slope is difficult to accurately discern from that plot. This is more easily accomplished by reference to a derivative plot.

Referring to FIG. 3, there is illustrated the first time derivative plot of the voltage versus time of line 30, identified by reference numeral 32. The steep, initial part of line 30 may reflect the presence of a native oxide layer. Each point of inflection of line 32, identified by reference numerals 32a-32o, approximately represents a change of the anodization front from one layer to another layer. The change from one layer to another is not exact because of interdiffusion and the rounding of the curves is an indication of the lack of a sharp interface. The distance along the time axis between a positive point of inflection, such as 32a and the adjacent negative point of inflection 32b provides a measure of the thickness of that layer in real time dimensions, as do the other plots described herein. In order to calculate the thickness of that layer, it is then only necessary to know the anodization rate (eg., angstroms/second) through that layer. This rate can be easily determined by performing a calibration to determine the speed at which the anodization front proceeds through that type of material under the particular anodization conditions. Similarly, another calibration can be used to determine the thickness of the layer defined by the time it took the anodization front to pass from point 32b to point 32c. Since the anodization front proceeds faster through the niobium layers than for the tungsten layers, the distance 32ab refers to a niobium layer and the distance 32bc refers to a tungsten layer. The total thickness can be determined by summing the thickness of the individual layers. It is to be understood that this method is not exact. There may be some overshooting and interface effects that are not taken into account depending on the types of materials present in the structure and the type of interface. These effects could be taken into account in a more detailed analysis method.

Figure 4:
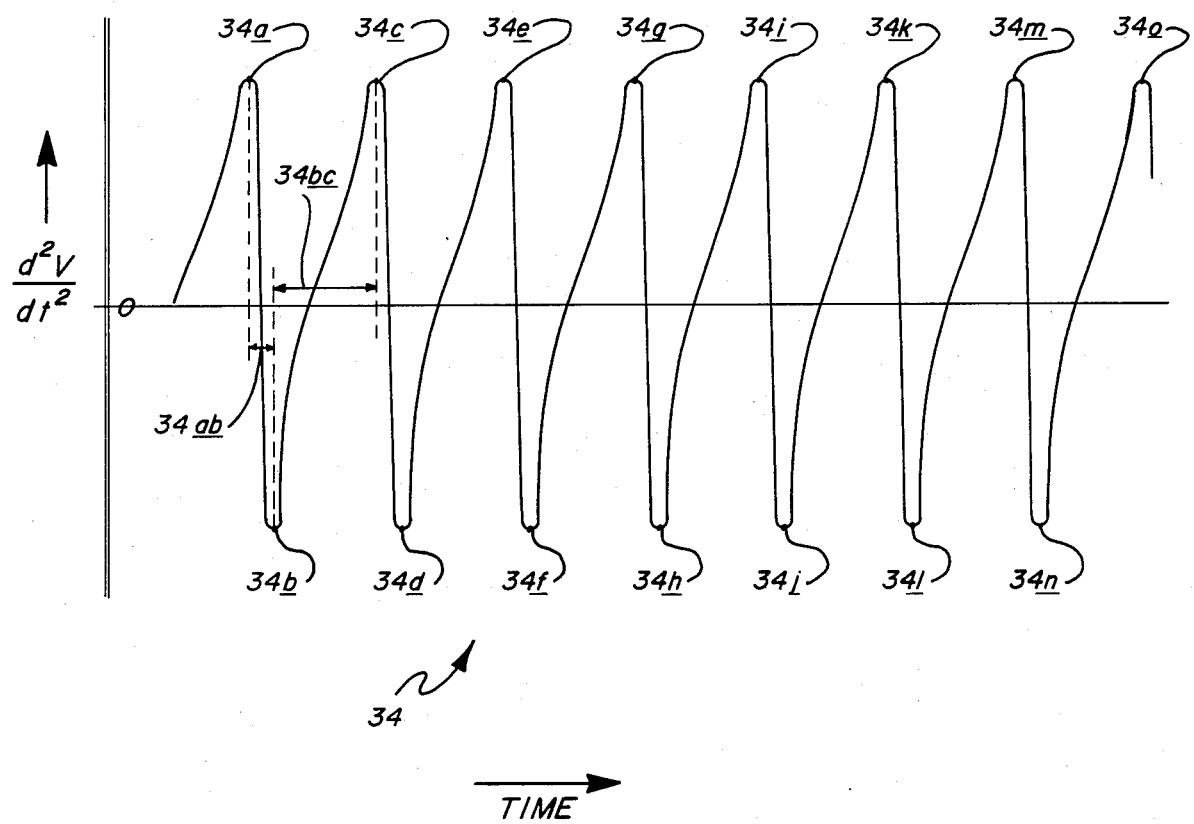
FIG. 4 is a graph illustrating the second time derivative of the anodization voltage as a function of time for the actual anodization of FIG. 2.

Referring to FIG. 4, there is illustrated the second time derivative plot of the anodization voltage as a function of time for the anodization plot 30 of FIG. 2 and is referred to by reference numeral 34. Each peak and valley of line 34, identified by reference numerals 34a-34o, identifies the points of inflection of line 32 and corresponds to the points of inflection 32a-32o previously identified in FIG. 3. The sample thickness can be determined from the distances between the points of inflection, as indicated by distances 34ab and 34bc, for example, as described with respect to FIG. 3.

While not wishing to be bound by theory, it is believed that the change in the anodization voltage is a result of the different resistivities of the oxides formed by the anodization as it proceeds through the different materials present from layer to layer in the multilayer structure. Other factors which affect the voltage may include the mobility of ions through the oxide, the dielectric constant of the oxide and the increase in the volume of the oxide compared to the original volume.

Preferably, in preparing a reference multilayer structure of known thickness for subsequent use as a standard, the layers are preferably prepared by the same method of preparation used for producing samples that are analyzed. In this type of analysis, it is desirable for the reference to have a similar type of layer to layer interface, since interdiffusion can affect the determination of the point where one layer ends and another begins. Also, the relative ratio of the layer thicknesses of the standard is preferably similar to that of the samples. Thus, for example, if the sample to be analyzed consists of equal thickness layers of material x and y, the standard preferably also consists of layers of equal thickness of x and y.

The number of layers, layer thickness and whether a particular multilayer structure has been degarded can be determined graphically as previously described, such as by reference to a plot of the anodization voltage versus time, the first time derivative of the anodization voltage as a function of time, or the second time derivative of the anodization voltage as a function of time. Other alternatives to the graphical determination would include, for example, various types of computer, mathematical and numerical techniques. Other techniques may also be available to analyze the data obtained by monitoring the change of the anodization voltage or a time derivative thereof as a function of time as the anodization occurs through the layers. For example, the second time derivative could be measured directly by an appropriate electrical circuit, as known to those skilled in the art.

Referring to FIG. 5, illustrated are two plots, 36 and 38. Plot 36 is a plot of the first time derivative of the anodization voltage versus time for a reference multilayer structure having no degradation. Plot 38 illustrates a plot of the first time derivative of the anodization voltage versus time for a sample having similar material and layers to the reference multilayer structure from which plot 36 was derived, except that the sample for plot 38 was annealed at 300° C. for one hour. The time derivative voltage modulation of plot 36, as defined by reference numeral 36a, is substantially greater than the time derivative voltage modulation of plot 38 as indicated by reference numeral 38a. This is an indication of heat degradation of interdiffusion between the individual layers of the sample which plot 38 represents. The relative height or modulation difference of plots 36 and 38 represents a semiquantitative measurement of the degree of degradation or the sharpness of the layer interfaces of the sample.

While the difference in modulation between normal and degraded structures has been described with respect to the modulation of the first time derivative of the anodization voltage versus time, a decrease in the modulation also exists for the anodization voltage versus time as well as its second time derivative. Analysis of this data may also be done to semiquantitatively determine degradation by determining the relative amount of modulation decrease.

Standards can be obtained in several ways. They can be made making samples by techniques having well characterized calibrations and various types of in-situ deposition monitors can be used. Also, the samples can be characterized by using several different techniques (such as Auger, X-ray diffraction and the methods described herein). When similar results are achieved, a high degree of confidence is obtained.

EXAMPLE 1

A multilayer sample consisting of alternating 20 angstrom nominal layers of niobium and tungsten was analyzed in accordance with the invention. The apparatus utilized was similar to that indicated in FIG. 1. The current source was adjusted to provide a constant current of 200 microamperes. The capacitor corresponding to capacitor 22 had a capacitance of 1 microfarad. The resistance of the resistor corresponding to resistor 24 had a resistance of 25,000 ohms. Electrolyte from a solution comprising 156 grams of ammonium pentaborate, 1,124 milliliters of ethylene glycol, 760 milliliters of water and enough sulfuric acid to obtain a pH of 3 was utilized. The surface area through which the anodization took place was about 0.079 $cm^2$ and a drop of electrolyte solution covered this area. The resulting plot of voltage versus time and the time derivative of voltage versus time and the second time derivative of voltage versus time are illustrated to FIGS. 2–4.

EXAMPLE 2

A reference sample was anodized as described in Example 1 with several differences. The resistance of resistor 24 was 50,000 ohms and the dc source of electric current 14 supplied 100 microamperes. The sample consisted of alternating layers of niobium and silicon, having a nominal layer thickness of 60 angstroms and 20 angstroms, respectively. Also, the pH of the electrolyte was about 6. The results of the anodization are illustrated as plot 36 of FIG. 5. A similar anodization was carried out on a similar sample except that the sample was annealed at 300° C. for one hour. The results of the anodization process are illustrated as plot 38 of FIG. 5.

EXAMPLE 3

A sample that consisted of alternting layers of titanium and tungsten was anodized in a manner similar to that described in Example 1.

The described technique is simple, inexpensive, and has excellent resolution (better than 10 angstroms).

While this invention has been described in relation to its preferred embodiments, it is to be understood that various modifications thereof will be apparent to those of ordinary skill in the art upon reading this specification and it is intended to cover all such modifications as fall within the scope of the appended claims.

We claim:

1. A method of determining whether degradation of an anodizable multilayer structure has occurred comprising:
   (a) applying an electrolytic anodizing voltage at constant current through a plurality of layers of said structure over a predetermined surface area of said structure to anodize said layers;
   (b) monitoring the change of the anodization voltage or a time derivative thereof as a function of time under a first set of conditions as the anodization progresses through said layers;
   (c) comparing the modulation of the anodization voltage or a time derivative thereof from Step (b) to the anodization voltage or time derivative thereof during anodization at constant current under similar conditions through a reference multilayer structure, similar to said anodizable multilayer structure and known to have no degradation, to determine whether degradation has occurred.

2. The method of claim 1 wherein the modulation of the anodization voltage as a function of time is compared.

3. The method of claim 1 wherein the modulation of the first time derivative of the anodization voltage as a function of time is compared.

4. The method of claim 1 wherein the modulation of the second time derivative of the anodization voltage as a function of time is compared.

5. The method of claim 1 wherein said multilayer structure comprises material selected from the group consisting of superconducting material and x-ray optics material.

6. The method of claim 1 wherein said multilayer structure comprises alternating layers of niobium and silicon.

7. The method of claim 1 wherein said multilayer structure comprises alternating layers of tungsten and silicon.

8. The method of claim 1 wherein said multilayer structure comprises alternating layers of hafnium and silicon.

9. The method of claim 1 wherein said multilayer structure comprises alternating layers selected from the group consisting of: niobium and tungsten; and titanium and tungsten.

10. The method of claim 1 wherein the layer thickness of said multilayer structure is in the range of from about 5 to about 25 angstroms.

11. A method of determining the number of layers of an anodizable multilayer structure comprising:
    (a) applying an electrolytic anodizing voltage at constant current through the layers of said structure over a predetermined surface area of said structure to anodize said layers;
    (b) monitoring the change of the anodization voltage or a time derivative thereof as a function of time as the anodization progresses through said plurality of layers;
    (c) analyzing changes in said anodization voltage from one layer into another layer to determine the number of layers of said multilayer structure.

12. The method of claim 11 wherein the anodization voltage as a function of time is analyzed.

13. The method of claim 11 wherein the first time derivative of the anodization voltage as a function of time is analyzed.

14. The method of claim 11 wherein the second time derivative of the anodization voltage as a function of time is analyzed.

15. The method of claim 11 wherein said multi-layer structure comprises material selected from the group consisting of superconducting material and x-ray optics material.

16. The method of claim 11 wherein said multi-layer structure comprises alternating layers of niobium and silicon.

17. The method of claim 11 wherein said multi-layer structure comprises alternating layers of tungsten and silicon.

18. The method of claim 11 wherein said multi-layer structure comprises alternating layers of hafnium and silicon.

19. The method of claim 11 wherein said multilayer structure comprises alternating layers selected from the group consisting of: niobium and tungsten; and titanium and tungsten.

20. The method of claim 11 wherein the layer thickness of said multilayer structure is in the range of from about 5 to about 25 angstroms.

21. A method of determining the thickness of an anodizable multilayer structure comprising:
 (a) applying an electrolytic anodizing voltage at constant current through the layers of said structure over a predetermined surface area of said structure to anodize said layers;
 (b) monitoring the change of the anodization voltage or a time derivative thereof as a function of time as the anodization progresses through said layers to obtain data;
 (c) determining the thickness of the multilayer structure by comparing the data to reference data obtained under similar conditions from a sample of known thickness.

22. The method of claim 21 wherein the known sample is a multilayer structure of the same material as said anodizable multilayer structure.

23. The method of claim 21 wherein the anodization voltage as a function of time is compared.

24. The method of claim 21 wherein the first time derivative of the anodization voltage as a function of time is compared.

25. The method of claim 21 wherein the second time derivative of the anodization voltage as a function of time is compared.

26. The method of claim 21 wherein said multilayer structure comprises material selected from the group consisting of superconducting material and x-ray optics material.

27. The method of claim 21 wherein said multilayer structure comprises alternating layers of niobium and silicon.

28. The method of claim 21 wherein said multilayer structure comprises alternating layers of tungsten and silicon.

29. The method of claim 21 wherein said multilayer structure comprises alternating layers of hafnium and silicon.

30. The method of claim 21 wherein said multilayer structure comprises alternating layers selected from the group consisting of: niobium and tungsten; and titanium and tungsten.

31. The method of claim 21 wherein the layer thickness of said multilayer structure is in the range of from about 5 to about 25 angstroms.

* * * * *